United States Patent
Wu et al.

(10) Patent No.: US 7,387,978 B2
(45) Date of Patent: Jun. 17, 2008

(54) SELECTIVE PARA-XYLENE PRODUCTION VIA METHYLATION OF TOLUENE WITH METHANOL IN THE PRESENCE OF MODIFIED HZSM-5 CATALYST

(75) Inventors: An-hsiang Wu, Kingwood, TX (US); Charles A. Drake, Nowata, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 11/334,245

(22) Filed: Jan. 18, 2006

(65) Prior Publication Data
US 2006/0122052 A1 Jun. 8, 2006

Related U.S. Application Data

(62) Division of application No. 10/453,679, filed on Jun. 3, 2003, now Pat. No. 7,049,260.

(51) Int. Cl.
B01J 29/87 (2006.01)
B01J 29/06 (2006.01)
C07C 2/64 (2006.01)
C07C 15/067 (2006.01)
C07C 5/22 (2006.01)

(52) U.S. Cl. .............. 502/60; 502/63; 502/64; 502/71; 502/77; 585/446; 585/470; 585/477

(58) Field of Classification Search ......... 585/446, 585/470, 477; 502/63, 64, 71, 77
See application file for complete search history.

(56) References Cited

U.S. PATENT DOCUMENTS

| | | | |
|---|---|---|---|
| 4,100,215 A * | 7/1978 | Chen | 585/454 |
| 4,927,979 A | 5/1990 | Yamagishi et al. | |
| 5,220,086 A | 6/1993 | Rodewald | |
| 5,371,312 A | 12/1994 | Lago et al. | |
| 5,403,800 A | 4/1995 | Beck et al. | |
| 5,455,213 A | 10/1995 | Chang et al. | |
| 5,476,823 A | 12/1995 | Beck et al. | |
| 5,495,059 A | 2/1996 | Beck et al. | |
| 5,498,814 A | 3/1996 | Chang et al. | |
| 5,516,736 A | 5/1996 | Chang et al. | |
| 5,541,146 A | 7/1996 | Chang et al. | |
| 5,552,357 A | 9/1996 | Lago et al. | |
| 5,571,768 A | 11/1996 | Chang et al. | |
| 5,574,199 A | 11/1996 | Beck et al. | |
| 5,602,066 A | 2/1997 | Beck et al. | |
| 5,607,888 A | 3/1997 | Chang et al. | |
| 5,610,112 A | 3/1997 | Lago et al. | |
| 5,612,270 A | 3/1997 | Beck et al. | |
| 5,675,047 A | 10/1997 | Beck et al. | |
| 5,905,051 A | 5/1999 | Wu et al. | |
| 6,051,519 A | 4/2000 | Wu et al. | |
| 6,084,096 A | 7/2000 | Li et al. | |
| 6,346,498 B1 | 2/2002 | Chang et al. | |
| 6,486,373 B1 | 11/2002 | Abichandani et al. | |
| 7,049,260 B2 * | 5/2006 | Wu et al. | 502/63 |
| 2006/0128556 A1 * | 6/2006 | Wu et al. | 502/71 |

FOREIGN PATENT DOCUMENTS

DE 10035604 3/2001
GB 1574523 9/1980

OTHER PUBLICATIONS

International Search Report, PCT/US04/017243, Dec. 14, 2004, 8 pages.

* cited by examiner

*Primary Examiner*—J. A. Lorengo
*Assistant Examiner*—Patricia L. Hailey
(74) *Attorney, Agent, or Firm*—Daniel E. Burke; David W. Dockter

(57) ABSTRACT

We disclose a method for converting toluene to xylenes, comprising contacting toluene with methanol in the presence of a silica-bound HZSM-5 catalyst. As an example, in one embodiment the method can include: (i) first silylating HZSM-5, to form silylated HZSM-5; (ii) first calcining the silylated HZSM-5, to form calcined silylated HZSM-5; (iii) binding the calcined silylated HZSM-5 to silica, to form silica-bound calcined silylated HZSM-5; (iv) extruding the silica-bound calcined silylated HZSM-5, to form extruded silica-bound calcined silylated HZSM-5; (v) second calcining the extruded silica-bound calcined silylated HZSM-5, to form extruded silica-bound twice-calcined silylated HZSM-5; (vi) second silylating the extruded silica-bound twice-calcined silylated HZSM-5, to form extruded silica-bound twice-calcined twice-silylated HZSM-5; and (vii) third calcining the extruded silica-bound twice-calcined twice-silylated HZSM-5, to form the silica-bound HZSM-5 catalyst.

20 Claims, No Drawings

SELECTIVE PARA-XYLENE PRODUCTION VIA METHYLATION OF TOLUENE WITH METHANOL IN THE PRESENCE OF MODIFIED HZSM-5 CATALYST

This application is a Divisional Application of U.S. patent application Ser. No. 10/453,679, filed Jun. 3, 2003, now U.S. Pat. No. 7,049,260 which is herein incorporated by reference in its entirety.

BACKGROUND OF THE INVENTION

The present invention relates generally to the field of xylenes production. More particularly, it concerns methods for converting toluene to xylenes using catalyst systems capable of producing p-xylene in high yield.

Methylation of toluene with methanol is known in the art as a useful technique for the formation of xylenes. The reaction has the following general formula (Formula I):

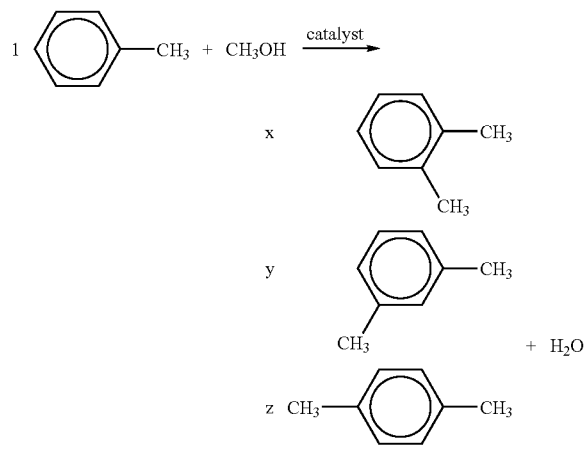

wherein x, y, and z are each between 0 and 1, inclusive, and x+y+z=1.

From top to bottom on the right of Formula I are ortho-xylene (o-xylene, 1,2-dimethylbenzene), meta-xylene (m-xylene, 1,3-dimethylbenzene), and para-xylene (p-xylene, 1,4-dimethylbenzene). Of the three, p-xylene is particularly useful in making, either directly or by substitution at the methylene moieties, straight-chain polymers such as polyethylene terephthalate (PET). Generally, however, the methylation of toluene produces all three of the xylene isomers shown in Formula I. Although the separation of p-xylene from a raw product mixture containing the other xylene isomers is possible, it will be apparent that techniques for maximizing the fraction of the raw product mixture defined by p-xylene (i.e., increasing z in Formula I) are beneficial.

SUMMARY OF THE INVENTION

In one embodiment, the present invention relates to a method for converting toluene to xylenes, comprising contacting toluene with methanol in the presence of a silica-bound HZSM-5 catalyst.

In another embodiment, the present invention relates to a method for converting toluene to xylenes, comprising contacting toluene with methanol in the presence of a silica-bound HZSM-5 catalyst, wherein the catalyst can be prepared by a process comprising: (i) first silylating HZSM-5, to form silylated HZSM-5; (ii) first calcining the silylated HZSM-5, to form calcined silylated HZSM-5; (iii) binding the calcined silylated HZSM-5 to silica, to form silica-bound calcined silylated HZSM-5; (iv) extruding the silica-bound calcined silylated HZSM-5, to form extruded silica-bound calcined silylated HZSM-5; (v) second calcining the extruded silica-bound calcined silylated HZSM-5, to form extruded silica-bound twice-calcined silylated HZSM-5; (vi) second silylating the extruded silica-bound twice-calcined silylated HZSM-5, to form extruded silica-bound twice-calcined twice-silylated HZSM-5; and (vii) third calcining the extruded silica-bound twice-calcined twice-silylated HZSM-5, to form the silica-bound HZSM-5 catalyst.

In a further embodiment, the present invention relates to a method for converting toluene to xylenes, comprising contacting toluene with methanol in the presence of a silica-bound HZSM-5 catalyst, wherein the catalyst can be prepared by a process comprising: (i) binding HZSM-5 to silica, to form silica-bound HZSM-5; (ii) silylating the silica-bound HZSM-5, to form silylated silica-bound HZSM-5; (iii) calcining the silylated silica-bound HZSM-5, to form calcined silylated silica-bound HZSM-5; (iv) first washing the calcined silylated silica-bound HZSM-5, to form washed calcined silylated silica-bound HZSM-5; (v) first drying the washed calcined silylated silica-bound HZSM-5, to form dried calcined silylated silica-bound HZSM-5; (vi) steaming the dried calcined silylated silica-bound HZSM-5, to form steamed calcined silylated silica-bound HZSM-5; (vii) treating the steamed calcined silylated silica-bound HZSM-5 with acid, to form acid-treated calcined silylated silica-bound HZSM-5; (viii) second washing the acid-treated calcined silylated silica-bound HZSM-5, to form washed acid-treated calcined silylated silica-bound HZSM-5; and (ix) second drying the washed acid-treated calcined silylated silica-bound HZSM-5, to form the silica-bound HZSM-5 catalyst.

Other aspects and features of the invention will become apparent in light of the detailed description and the claims.

DESCRIPTION OF ILLUSTRATIVE EMBODIMENTS

In one embodiment, the present invention relates to a method for converting toluene to xylenes, comprising: (a) contacting toluene with methanol in the presence of a silica-bound HZSM-5 catalyst. The catalyst of the present invention can be prepared by a number of processes, three of which will be described below.

Techniques for contacting toluene with methanol in the presence of a solid catalyst for the production of xylenes are well known in the art. (The term "xylenes," when used without an isomer-designating prefix, refers herein to a mixture of ortho-, meta-, and para-xylenes). Any of a number of well known methods can be used for producing xylenes in light of the present disclosure, and the invention is not limited by the particular method and reaction parameters used.

HZSM-5 is known in the art. ZSM-5 is an aluminosilicate zeolite with a high silica content and a low aluminum content. Its structure can be considered to comprise channels with intersecting tunnels. The aluminum sites are generally acidic, due to the substitution of $Al^{3+}$ in place of tetrahedral $Si^{4+}$ silica requiring the presence of an added positive charge. When this positive charge is provided by $H^+$, the zeolite is termed HZSM-5.

HZSM-5 is commercially available from Süd-Chemie Inc., Louisville, Ky., among other sources.

In one embodiment, the catalyst can be prepared by a process comprising (i) binding the HZSM-5 to silica, to form the silica-bound HZSM-5. "Binding" in this context, as used herein, generally refers to physically admixing HZSM-5 and silica in such a manner that the silica provides a support for the HZSM-5. The proportion of HZSM-5 in the admixture, as a weight percentage of HZSM-5 and silica, can be from about 1 wt % to about 90 wt %. In one embodiment, the proportion of HZSM-5 in the admixture can be from about 2 wt % to about 50 wt %.

Silica is well known in the art and commercially available from a number of suppliers.

The silica-bound HZSM-5 catalyst prepared according to this embodiment can catalyze the methylation of toluene to xylenes with a para-xylene selectivity in the range of about 65% to 100% of all xylenes produced (the percentages can be interchangeably expressed by mole fraction or by mass).

In another embodiment, the present invention relates to a method for converting toluene to xylenes, comprising:

(a) contacting toluene with methanol in the presence of a silica-bound HZSM-5 catalyst, wherein the catalyst can be prepared by a process comprising: (i) first silylating HZSM-5, to form silylated HZSM-5; (ii) first calcining the silylated HZSM-5, to form calcined silylated HZSM-5; (iii) binding the calcined silylated HZSM-5 to silica, to form silica-bound calcined silylated HZSM-5; (iv) extruding the silica-bound calcined silylated HZSM-5, to form extruded silica-bound calcined silylated HZSM-5; (v) second calcining the extruded silica-bound calcined silylated HZSM-5, to form extruded silica-bound twice-calcined silylated HZSM-5; (vi) second silylating the extruded silica-bound twice-calcined silylated HZSM-5, to form extruded silica-bound twice-calcined twice-silylated HZSM-5; and (vii) third calcining the extruded silica-bound twice-calcined twice-silylated HZSM-5, to form the silica-bound HZSM-5 catalyst.

The HZSM-5 is as described above.

In the first silylating step, the HZSM-5 can be silylated to form silylated HZSM-5.

"Silylating," as used herein, refers to the treating of HZSM-5 with silicon compounds selected from the group of alkoxysilanes and polysiloxanes.

An alkoxysilane consists of compounds having the formula $Si(R'_n)(OR)_{(4-n)}$, wherein n is an integer from 0-3, inclusive, each R and R' is independently a $C_1$-$C_6$ alkyl group or a phenyl group. Such alkoxysilanes can be tetramethoxysilane, tetraethoxysilane, tetrapropoxysilane, tetrabutoxysilane, tetraisopropoxysilane, tetraisobutoxysilane and tetrasecbutoxysilane. Exemplary alkoxysilanes include, but are not limited to, tetraethoxysilane (TEOS), among others.

A polysiloxane consists of compounds having the formula $Si(R'_x)(OR)_{(3-x)}[Si(R'_y)(OR)_{(2-y)}]_nOSi(R'_z)(OR)_{(3-z)}$, wherein x and z are an inte 0-3, inclusive, y is an integer from 0-2, inclusive, n is the degree of polymerization, and each R and R' is independently a $C_1$-$C_6$ alkyl group or a phenyl group. Polysiloxanes consist of organosubstituted polysiloxane compounds of varying degrees of polymerization. The only requirement regarding degrees of polymerization, for the instant process, is that the viscosity of the fluid be such that the HZSM-5 can be adequately mixed with the polysiloxane to insure good contact.

The polysiloxanes can be totally methylated fluids or methyl and phenyl substituted fluids. The polysiloxanes can be either linear or cyclic in structure. The polysiloxanes can be dimethyl and methylphenyl substituted copolymers.

The polysiloxanes can be, for example, trimethylsilyl end-blocked methyl and phenyl substituted polysiloxanes, trimethylsilyl end-blocked dimethylpolysiloxanes, methylphenylhydroxysilyl end-blocked methyl and phenyl substituted polysiloxanes dimethylcyclopolysiloxanes, and methyl and phenyl substituted cyclopolysiloxanes. Exemplary polysiloxanes include, but are not limited to poly(methyl phenyl) siloxane (PMPS), among others.

In a silylating step, the HZSM-5 can be contacted with the alkoxysilane according to any appropriate technique, such as a batch or continuous process; with the alkoxysilane in the vapor, liquid, or solid phase; among others. If the alkoxysilane is provided in the vapor phase, a carrier or diluent gas, such as nitrogen, helium, argon, carbon dioxide, air, or steam, among others, can be used. The alkoxysilane concentration in the gas (as vol % relative to the total volume of the gases) can be from about 0.1 vol % to 100 vol %. If the alkoxysilane is provided in the liquid phase, a solvent, such as benzene, toluene, xylenes, pentane, hexane, heptane, octane, methanol, ethanol, or propanol, among others, can be used. The alkoxysilane concentration in the solution (as wt % relative to the total weight of the gases) can be from about 0.1 wt % to about 10 wt %. Selecting a particular diluent gas or solvent is a matter of routine experimentation for the skilled artisan.

A silylating step can be performed at any suitable temperature and for any suitable duration. A suitable temperature for silylating with gas phase alkoxysilane can be from about 10° C. to about 600° C., and with liquid phase alkoxysilane, from about 10° C. to about 150° C. The duration of silylating can be up to about 1 hr, up to about 2 hr, up to about 3 hr, up to about 6 hr, up to about 12 hr, up to about 18 hr, up to about 24 hr, up to about 36 hr, up to about 48 hr, up to about 72 hr, or more than about 72 hr. In one embodiment, the duration of silylating is at least about 6 hr.

The amount of the alkoxysilane used to silylate the HZSM-5 can vary. In one embodiment, the amount of the alkoxysilane (on a weight basis of silicon to the weight of the HZSM-5) to be introduced to the HZSM-5 can be from about 1 wt % to about 10 wt % (i.e., from about 1 g Si as alkoxysilane per 100 g HZSM-5 to about 10 g Si as alkoxysilane per 100 g HZSM-5).

In one embodiment, the first silylating step comprises silylating the HZSM-5 with tetraethoxysilane (TEOS).

The product of the first silylating step is a silylated HZSM-5.

In the first calcining step, the silylated HZSM-5 can be calcined to form calcined silylated HZSM-5.

"Calcining," as used herein, refers to the treatment of a material with heat under an oxidizing environment. The amount of heat applied can be up to any relatively high temperature, such as about 200° C. or higher, about 300° C. or higher, about 400° C. or higher, about 500° C. or higher, or about 600° C. or higher. In one embodiment, calcining is performed at a temperature from about 500° C. to about 600° C. An "oxidizing environment" is any environment, typically a gas, under which carbon atoms present in the material can be reacted with compounds in the environment to form carbon dioxide. Typically, the oxidizing environment comprises gaseous oxygen or gaseous air. The duration of the calcining step is not critical and can be adjusted by the skilled artisan having the benefit of the present disclosure.

The product of the first calcining step is calcined silylated HZSM-5.

In the binding step, the calcined silylated HZSM-5 can be bound to silica, to form silica-bound calcined silylated HZSM-5. The binding step can be performed as described above, with the portions of calcined silylated HZSM-5 and silica described above.

In the extruding step, the silica-bound calcined silylated HZSM-5 can be extruded to form extruded silica-bound calcined silylated HZSM-5.

"Extruding," as used herein, involves the molding of a liquid, powder, or otherwise moldable material into a rigid solid form. Extruding can involve the use of heat or pressure. The term "extruding" encompasses both batchwise molding techniques and continuous molding techniques. In one embodiment, the extruding step comprises producing a 1/16 inch diameter solid extrudate and pelletizing the extrudate.

The product of the extruding step is extruded silica-bound calcined silylated HZSM-5.

In the second calcining step, the extruded silica-bound calcined silylated HZSM-5 is calcined to form extruded silica-bound twice-calcined silylated HZSM-5. Calcining has been described above.

In the second silylating step, the extruded silica-bound twice-calcined silylated HZSM-5 can be silylated to form extruded silica-bound twice-calcined twice-silylated HZSM-5. Silylating has been described above. In one embodiment, the second silylating step comprises silylating the HZSM-5 with poly(methyl phenyl) siloxane (PMPS).

In the third calcining step, the extruded silica-bound twice-calcined twice-silylated HZSM-5 can be calcined to form the silica-bound HZSM-5 catalyst. The silica-bound HZSM-5 catalyst prepared according to this embodiment can catalyze the methylation of toluene to xylenes with a para-xylene selectivity in the range of about 65% to 100%, such as about 85%, of all xylenes produced.

In a further embodiment, the present invention relates to a method for converting toluene to xylenes, comprising (a) contacting toluene with methanol in the presence of a silica-bound HZSM-5 catalyst, wherein the catalyst can be prepared by a process comprising: (i) binding HZSM-5 to silica, to form silica-bound HZSM-5; (ii) silylating the silica-bound HZSM-5, to form silylated silica-bound HZSM-5; (iii) calcining the silylated silica-bound HZSM-5, to form calcined silylated silica-bound HZSM-5; (iv) first washing the calcined silylated silica-bound HZSM-5, to form washed calcined silylated silica-bound HZSM-5; (v) first drying the washed calcined silylated silica-bound HZSM-5, to form dried calcined silylated silica-bound HZSM-5; (vi) steaming the dried calcined silylated silica-bound HZSM-5, to form steamed calcined silylated silica-bound HZSM-5; (vii) treating the steamed calcined silylated silica-bound HZSM-5 with acid, to form acid-treated calcined silylated silica-bound HZSM-5; (viii) second washing the acid-treated calcined silylated silica-bound HZSM-5, to form washed acid-treated calcined silylated silica-bound HZSM-5; and (ix) second drying the washed acid-treated calcined silylated silica-bound HZSM-5, to form the silica-bound HZSM-5 catalyst.

In the binding step, the HZSM-5 can be bound to silica, to form silica-bound HZSM-5. The binding of HZSM-5 to silica has been described above.

In the silylating step, the silica-bound HZSM-5 can be silylated to form silylated silica-bound HZSM-5. Silylating has been described above. Any alkoxysilane can be used. In one embodiment, the silylating step comprises contacting the silica-bound HZSM-5 with PMPS. The product of the silylating step is a silylated silica-bound HZSM-5.

In the calcining step, the silylated silica-bound HZSM-5 can be calcined to form calcined silylated silica-bound HZSM-5. Calcining has been described above.

In the first washing step, the calcined silylated silica-bound HZSM-5 can be washed to form washed calcined silylated silica-bound HZSM-5.

"Washing," as used herein, refers to the application of a liquid, such as water, a water-surfactant solution, or an organic solvent, to a material. The washing can involve one or more applications of the liquid to the material, and can involve one or more soaking applications followed by one or more rinsing applications, or one or more combined soaking/rinsing applications, among other possibilities that will recommend themselves to the skilled artisan having the benefit of the present disclosure. Washing can be performed at ambient temperature and pressure or adjusted to higher or lower temperature, higher or lower pressure, or both.

The product of the first washing step is a washed calcined silylated silica-bound HZSM-5.

In the first drying step, the washed calcined silylated silica-bound HZSM-5 can be dried to form dried calcined silylated silica-bound HZSM-5.

"Drying," as used herein subsequent to washing, refers to the evaporation, either passive or forced, of a liquid used in washing from a material. Forced evaporation can include the use of heat, forced air, or desiccant materials, among other materials or techniques.

The product of the first drying step is dried calcined silylated silica-bound HZSM-5.

In the steaming step, the dried calcined silylated silica-bound HZSM-5 can be steamed to form steamed calcined silylated silica-bound HZSM-5.

"Steaming," as used herein, refers to contacting a material with a gas mixture comprising water vapor and wherein the gas mixture has a temperature of greater than about 100° C., such as from about 500° C. to about 700° C. The duration of the steaming step is not critical. Typical durations of the steaming step can be from about 3 hr to about 12 hr. Generally, though not to be bound by theory, the use of higher temperatures, longer durations, or both in the steaming step will lead to greater dealuminumization in the catalyst. In one embodiment, the steaming step comprises the use of a gas mixture consisting essentially of water vapor at 600° C. for a duration of about 6 hr.

The product of the steaming step is a steamed calcined silylated silica-bound HZSM-5.

In the treating step, the steamed calcined silylated silica-bound HZSM-5 can be treated with acid, to form acid-treated calcined silylated silica-bound HZSM-5.

"Treating with acid," as used herein, refers to the contacting of a material with an acidic solution, i.e., an aqueous solution comprising an acid and having a pH of less than 7. Any mineral or organic acid can be used. In one embodiment, the acid can be a mineral acid. In one embodiment, the mineral acid can be hydrochloric acid (HCl). In one embodiment, the acidic solution comprises from about 1 wt % HCl to saturation with HCl (about 38 wt %). In one embodiment, in the treating step the acid can be hydrochloric acid at about 0.1 N in aqueous solution.

The temperature, duration, and other parameters of the treating step are not critical. Generally, the temperature can be from about room temperature to about 100° C., and the duration can be from about 1 hr to about 48 hr, such as from about 6 hr to about 24 hr. In one embodiment, the treating step is performed at about 90° C. for about 16 hr.

The product of the treating step is an acid-treated calcined silylated silica-bound HZSM-5.

In the second washing step, the acid-treated calcined silylated silica-bound HZSM-5 is washed to form washed acid-treated calcined silylated silica-bound HZSM-5. The washing step can be performed as is described above.

In the second drying step, the washed acid-treated calcined silylated silica-bound HZSM-5 can be dried to form the silica-bound HZSM-5 catalyst. The drying step can be performed as is described above.

The silica-bound HZSM-5 catalyst prepared according to this embodiment can catalyze the methylation of toluene to xylenes with a para-xylene selectivity in the range of about 65% to 100%, such as essentially 100%, of all xylenes produced.

The following examples are included to illustrate particular embodiments of the invention. However, those of skill in the art should, in light of the present disclosure, appreciate that many changes can be made in the specific embodiments which are disclosed and still obtain a like or similar result without departing from the spirit and scope of the invention.

EXAMPLE 1

HZSM-5 zeolite was bound to silica (Ludox AS-40) by admixing, and extruded (1/16 in pellets). The extruded material was calcined (538° C., 6 hr). The silica-bound HZSM-5 (13.4 g) was silylated with 26.8 g of a 10 wt % poly(methyl phenyl) siloxane (PMPS) solution in cyclohexane. Thereafter, the product was calcined at 538° C. for 6 hr; washed in water; and dried (538° C., 2 hr). 13.7 g of dried calcined silylated silica-bound HZSM-5 were produced. An aliquot (6.0 g) of the dried calcined silylated silica-bound HZSM-5 was then subjected to 100% steam, 600° C., for 6 hr. After steaming, the composition was treated with 200 g 0.1 N HCl at 90° C. for 16 hr; washed in water; and dried (538° C., 2 hr). A total of 6.0 g of silica-bound HZSM-5 catalyst was prepared (as a 1/16 inch extrudate).

Thereafter, the catalyst was used to catalyze the methylation of toluene by methanol. The catalyst was charged to a reactor, and feeds commenced of 20 wt % methanol/80 wt % toluene (20 mL/hr) and hydrogen (260 mL/min). The reactor was maintained at about 600° C. and a pressure of about 70-80 psig. The reaction was allowed to proceed for about 7.5 hr, with product quantities measured during the run by GC-FID.

Table 1 presents the percentage conversion of methanol (i.e., the weight percentage of all methanol added to the reactor minus the weight percentage of methanol present in the reactor), the weight percentage yield of all xylenes (i.e., the weight of all xylenes present divided by the weight of all methanol and toluene added to the reactor, multiplied by 100%), and the selectivity of para-xylene (the weight of para-xylene divided by the weight of all xylenes present, multiplied by 100%) at four time points.

TABLE 1

| Time (hr) | Methanol conversion (wt %) | Total xylenes yield (wt %) | Para-xylene selectivity (wt %) |
|---|---|---|---|
| 3.25 | 100.0 | 11.5 | 100.0 |
| 4.75 | 100.0 | 11.3 | 100.0 |
| 6.00 | 100.0 | 10.7 | 100.0 |
| 7.50 | 100.0 | 10.7 | 100.0 |

Table 1 indicates that essentially complete selectivity to para-xylene in the methylation of toluene is possible by the use of a catalyst of the present invention.

EXAMPLE 2

HZSM-5 zeolite was silylated with a 10% solution of tetraethyl orthosilicate (TEOS), and then was calcined at 538° C. for 6 hr. The calcined silylated HZSM-5 was then bound to silica (Ludox AS-40) by admixing, and extruded (1/16 inch pellets). The extruded material was again calcined (538° C. for 6 hr). The calcined extruded material was silylated with a 10 wt % poly(methyl phenyl) siloxane (PMPS) (Dow 510) solution in cyclohexane and third calcined (538° C. for 6 hr) to produce the silica-bound HZSM-5 catalyst of this example.

Thereafter, the catalyst was used to catalyze the methylation of toluene by methanol. The catalyst was charged to a reactor, and feeds commenced of 20 wt % methanol/80 wt % toluene (20 mL/hr) and hydrogen (260 mL/min). The reactor was maintained at about 600° C. and a pressure of about 70-86 psig. The reaction was allowed to proceed for about 7 hr, with product quantities measured during the run by GC-FID.

At the end of the reaction duration, it was discovered that the reaction exhibited methanol conversion of 99.7 wt % of added methanol; total xylenes yield of 21.5 wt % of added methanol plus added toluene; and para-xylene selectivity of 84.6 wt % of total xylenes.

This example indicates that methylation of toluene with use of a catalyst of the present invention can produce para-xylene with high selectivity.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for converting toluene to xylenes, comprising:
   (a) contacting toluene with methanol in the presence of a silica-bound HZSM-5 catalyst, wherein the catalyst is prepared by a process comprising:
      (i) first silylating HZSM-5 with an alkoxysilane, to form silylated HZSM-5;
      (ii) first calcining the silylated HZSM-5, to form calcined silylated HZSM-5;
      (iii) binding the calcined silylated HZSM-5 to silica, to form silica-bound calcined silylated HZSM-5;
      (iv) extruding the silica-bound calcined silylated HZSM-5, to form extruded silica-bound calcined silylated HZSM-5;
      (v) second calcining the extruded silica-bound calcined silylated HZSM-5, to form extruded silica-bound twice-calcined silylated HZSM-5;
      (vi) second silylating the extruded silica-bound twice-calcined silylated HZSM-5, to form extruded silica-bound twice-calcined twice-silylated HZSM-5; and
      (vii) third calcining the extruded silica-bound twice-calcined twice-silylated HZSM-5, to form the silica-bound HZSM-5 catalyst.

2. The method of claim 1, wherein the first silylating step comprises contacting the HZSM-5 with tetraethoxysilane (TEOS), and the second silylating step comprises contacting the extruded silica-bound twice-calcined silylated HZSM-5 with poly(methyl phenyl) siloxane (PMPS).

3. The method of claim 1, wherein the calcined silylated HZSM-5 in the binding step is present in an amount of about 1 wt % to about 90 wt % based on the total weight of calcined silylated HZSM-5 and silica.

4. The method of claim 1, wherein the alkoxysilane in the first silylating step is present in an amount of about 1 wt % to about 10 wt %, based on the weight of silicon to the weight of the HZSM-5.

5. The method of claim 1, wherein the alkoxysilane in the first silylating step is in a vapor, liquid, or solid phase.

6. The method of claim 1, wherein the alkoxysilane has the formula $Si(R'_n)(OR)_{(4-n)}$, wherein n is an integer from 0-3, inclusive, each R and R' is independently a $C_1$-$C_6$ alkyl group or a phenyl group.

7. The method of claim 1, wherein the second silylating step comprises contacting the extruded silica-bound twice-calcined silylated HZSM-5 with an alkoxysilane or polysiloxane.

8. The method of claim 7, wherein the polysiloxane has the formula $Si(R'_x)(OR)_{(3-x)}[Si(R'_y)(OR)_{(2-y)}]_nOSi(R'_z)(OR)_{(3-z)}$, wherein x and z are an integer from 0-3, inclusive, y is an integer from 0-2, inclusive, n is the degree of polymerization, and each R and R' is independently a $C_1$-$C_6$ alkyl group or a phenyl group.

9. The method of claim 7, wherein the polysiloxane is a trimethylsilyl end-blocked methyl substituted polysiloxane, trimethylsilyl end-blocked phenyl substituted polysiloxane, trimethylsilyl end-blocked dimethylpolysiloxane, methylphenylhydroxysilyl end-blocked methyl substituted polysiloxane, methylphenylhydroxysilyl end-blocked phenyl substituted polysiloxane, dimethylcyclopolysiloxane, methyl substituted cyclopolysiloxane, or phenyl substituted cyclopolysiloxane.

10. A method for converting toluene to xylene, comprising:
(a) contacting toluene with methanol in the presence of a silica-bound HZSM-5 catalyst, wherein the catalyst is prepared by a process comprising:
(i) binding HZSM-5 to silica, to form silica-bound HZSM-5;
(ii) silylating the silica-bound HZSM-5, to form silylated silica-bound HZSM-5;
(iii) calcining the silylated silica-bound HZSM-5, to form calcined silylated silica- bound HZSM-5;
(iv) first washing the calcined silylated silica-bound HZSM-5, to form washed calcined silylated silica-bound HZSM-5;
(v) first drying the washed calcined silylated silica-bound HZSM-5, to form dried calcined silylated silica-bound HZSM-5;
(vi) steaming the dried calcined silylated silica-bound HZSM-5, to form steamed calcined silylated silica-bound HZSM-5;
(vii) treating the steamed calcined silylated silica-bound HZSM-5 with acid, to form acid-treated calcined silylated silica-bound HZSM-5;
(viii) second washing the acid-treated calcined silylated silica-bound HZSM-5, to form washed acid-treated calcined silylated silica-bound HZSM-5; and
(ix) second drying the washed acid-treated calcined silylated silica-bound HZSM-5, to form the silica-bound HZSM-5 catalyst.

11. The method of claim 10, wherein the silylating step comprises contacting the silica-bound HZSM-5 with PMPS.

12. The method of claim 10, wherein in the treating step the acid is hydrochloric acid at about 0.1 N in aqueous solution.

13. The method of claim 10, wherein the treating step is performed at about room temperature to about 100° C. for about 12 hr to about 24 hr.

14. The method of claim 10, wherein the steaming step is performed with about 100% water vapor at about 500° C. to about 700° C. for about 3 hr to about 12 hr.

15. The method of claim 10, wherein the silylating step comprises contacting the silica-bound HZSM-5 with an alkoxysilane or polysiloxane.

16. The method of claim 15, wherein the polysiloxane has the formula $Si(R'_x)(OR)_{(3-x)}[Si(R'_y)(OR)_{(2-y)}]_nOSi(R'_z)(OR)_{(3-z)}$, wherein x and z are an integer from 0-3, inclusive, y is an integer from 0-2, inclusive, n is the degree of polymerization, and each R and R' is independently a $C_1$-$C_6$ alkyl group or a phenyl group.

17. The method of claim 15, wherein the alkoxysilane has the formula $Si(R'_n)(OR)_{(4-n)}$, wherein n is an integer from 0-3, inclusive, each R and R' is independently a $C_1$-$C_6$ alkyl group or a phenyl group.

18. The method of claim 10, wherein the steaming step comprises contacting the dried calcined silylated silica-bound HZSM-5 with a gas mixture comprising water vapor; and wherein the gas mixture has a temperature of greater than about 100° C.

19. The method of claim 10, wherein the treating step comprises contacting the steamed calcined silylated silica-bound HZSM-5 with an acidic solution; wherein the acidic solution has a pH of less than 7; and wherein acidic solution comprises a mineral or organic acid.

20. The method of claim 19, wherein the acidic solution comprises from about 1 wt % HCl to about 38 wt % HCl.

* * * * *